(12) United States Patent
Gutierrez

(10) Patent No.: US 8,573,207 B2
(45) Date of Patent: Nov. 5, 2013

(54) METHOD AND SYSTEM TO DETECT RESPIRATORY ASYNCHRONY

(75) Inventor: Guillermo Gutierrez, Fairfield, PA (US)

(73) Assignee: Guillermo Gutierrez, McLean, VA (US)

(*) Notice: Subject to any disclaimer, the term of this patent is extended or adjusted under 35 U.S.C. 154(b) by 130 days.

(21) Appl. No.: 13/232,206

(22) Filed: Sep. 14, 2011

(65) Prior Publication Data

US 2012/0073574 A1 Mar. 29, 2012

Related U.S. Application Data (60) Provisional application No. 61/387,204, filed on Sep. 28, 2010.

(51) Int. Cl.
*A61B 5/08* (2006.01)

(52) U.S. Cl.
USPC ............ 128/204.23; 128/204.21; 128/905; 128/920; 600/532

(58) Field of Classification Search
USPC .......... 128/204.21, 204.23, 204.26, 901, 902, 128/905, 920; 600/529, 532–534, 537–538, 600/543
See application file for complete search history.

(56) References Cited

U.S. PATENT DOCUMENTS

| | | | | |
|---|---|---|---|---|
| 7,094,206 | B2 * | 8/2006 | Hoffman | 600/529 |
| 2007/0032733 | A1 * | 2/2007 | Burton | 600/509 |
| 2008/0177195 | A1 * | 7/2008 | Armitstead | 600/529 |
| 2008/0269625 | A1 * | 10/2008 | Halperin et al. | 600/508 |
| 2009/0107502 | A1 * | 4/2009 | Younes | 128/204.23 |
| 2010/0016694 | A1 * | 1/2010 | Martin et al. | 600/324 |
| 2010/0152600 | A1 | 6/2010 | Droitcour et al. | |

FOREIGN PATENT DOCUMENTS

WO WO-2008/131798 A1 11/2008

OTHER PUBLICATIONS

International Search Report for PCT Application No. PCT/US11/53567, mailed Jan. 27, 2012, 2 pages.
Written Opinion for PCT Application No. PCT/US11/53567, mailed Jan. 27, 2012, 4 pages.

\* cited by examiner

*Primary Examiner* — Justine Yu
*Assistant Examiner* — Timothy Stanis
(74) *Attorney, Agent, or Firm* — Ralph P. Albrecht; ATFirm PLLC (57) ABSTRACT

A noninvasive of detecting patient-ventilator asynchrony that is easily adaptable to existing ventilator monitoring systems and provides timely and actionable information on the degree of patient asynchrony both during invasive and non-invasive ventilation. Display of, frequency spectra and the use of a measure of spectral organization, such as $H_1/DC$, allows for both manual and automatic adjustment of a ventilators to prevent or correct patient-ventilator asynchrony.

16 Claims, 9 Drawing Sheets

METHOD AND SYSTEM TO DETECT RESPIRATORY ASYNCHRONY

CROSS-REFERENCE TO RELATED APPLICATION

This application claims the benefit of U.S. Provisional Patent Application No. 61/387,204, filed on Sep. 28, 2010.

BACKGROUND OF THE INVENTION

Asynchronous events occur during mechanical ventilation when a patient's intrinsic respiratory rhythm fails to entrain to machine inflation or when ventilatory support is inadequate to meet the patient's requirements. Patient-ventilator asynchrony is a condition that affects a significant proportion of patients undergoing mechanical ventilation. It may be present either at the beginning of inspiration (trigger asynchrony), when the inspiratory efforts of the patient and the ventilator are out of phase. It also may be present during expiration should the inspiratory flow provided by the ventilator stop before or after the patient's own inspiratory effort. Patient-ventilator asynchrony is a common occurrence in mechanically ventilated patients, in particular those with acute or severe lung injury. Poorly synchronized patients may develop respiratory muscle fatigue, remain on mechanical ventilation longer and appear to have worse outcomes. As used herein patient includes any subject, and is not limited to humans.

Appropriate ventilatory support depends to a great extent on the reliable recognition of ventilator asynchrony; however, this is not a simple task. Perhaps the most reliable method presently available to detect asynchrony is the placement of a balloon catheter in the esophagus to measure intra-thoracic pressure changes during the breath cycle. Electromyography also has been used to assess asynchrony by comparing ventilatory muscle electrical activity to the initiation of ventilator-delivered inspiratory flow. Both methods have the obvious disadvantage of being invasive and not well tolerated by many patients, in particular those who are alert and awake. Further, they are relatively complex and require considerable operator experience. Non-invasive methods to establish the degree of patient-ventilator synchronicity have been proposed as possible alternatives to electromyography and measures of intrathoracic pressures. Perhaps the method with the widest clinical acceptance is the asynchrony index (AI) initially described by Varon J, Fromm R, Rodarte J, Reinoso M. "Prevalence of patient-ventilator asynchrony in critically ill patients." *Chest* 1994; 106:141S. Although useful as a research tool, the AI method is not easily applied to monitoring patient-ventilator asynchrony since it is laborious and operator dependent.

While assessing the incidence of patient-ventilator asynchrony during mechanical ventilation, one study found asynchrony in approximately 25% of patients. Thille A W, Rodriguez P, Cabello B, Lellouche F, Brochard L., "Patient-ventilator asynchrony during assisted mechanical ventilation." *Intensive Care Med.* 2006; 32:1515-1522. This condition was associated with significantly longer duration of mechanical ventilation. In a subsequent study they eliminated ineffective triggering in two-thirds of asynchronous cases by decreasing pressure support or inspiratory duration. More recently, the use of a neurally adjusted ventilator assist to control the timing and pressure of assisted delivery has been shown to decrease asynchrony by reducing triggering and cycling delays. Examples of two such studies are described in Spahija J, de Marchie M, Albert M, Bellemare P, Delisle S, Beck J, Sinderby C., "Patient-ventilator interaction during pressure support ventilation and neutrally adjusted ventilatory assist." *Crit. Care Med.* 2010; 38:518-526; and Terzi N, Pelieu I, Guittet L, Ramakers M, Seguin A, Daubin C, Charbonneau P, du Cheyron D, Lofaso F. "Neurally adjusted ventilatory assist in patients recovering spontaneous breathing after acute respiratory distress syndrome: Physiological evaluation." *Crit. Care Med.* 2010; 38:1830-1837.

Several noninvasive methods have been developed to automate the evaluation of asynchrony detection. These methods analyze airway signals searching for anomalies indicative of ineffective patient triggering (IT). Mulqueeny Q, Ceriana P, Carlucci A, Fanfulla F, Delmastro M, Nava S. "Automatic detection of ineffective triggering and double triggering during mechanical ventilation." *Int Care Med* 2007; 33:2014-2018 proposed applying a noise filter and an unintentional leak compensation algorithm to the flow and pressure curves, followed by the calculation of the first and second derivatives of the flow signal. They tested their method in twenty mechanically ventilated patients and found 91% sensitivity and 97% specificity when compared to the manually derived AI.

Cuvelier A, Achour L, Rabarimanantsoa H, Letellier C, Muir J-F, Fauroux B. "A noninvasive method to identify ineffective triggering in patients with noninvasive pressure support ventilation." *Respiration* 2010; 80:198-206, developed a complex algorithm that analyzed phase portraits, a geometrical depiction of temporal changes in patient-ventilator interaction. They were able to identify 95% of all IT efforts when comparing the results of this method to esophageal tracings in fourteen children with cystic fibrosis on non-invasive ventilation.

Chen C W, Lin W C, Hsu C H, Cheng K S, Lo C S. "Detecting ineffective triggering in the expiratory phase in mechanically ventilated patients based on airway flow and pressure deflection: feasibility of using a computer algorithm." *Crit. Care Med.* 2008; 36:455-461, developed a computerized algorithm based on small deflections of the flow and pressure signals during the expiratory phase of ventilation. The algorithm detected IT with high sensitivity and specificity in fourteen ventilated patients. This method has the disadvantage of detecting only one type of patient-ventilator interaction.

Younes M, Brochard L, Grasso S, Kun J, Mancebo J, Ranieri M, Richard J C, Younes H. "A method for monitoring and improving patient: ventilator interaction." *Intensive Care Med.* 2007; 33:1337-1346, monitored patient-ventilator interaction with a proprietary system that generates a signal mimicking respiratory muscle pressure output. The signal was derived from the equation of motion of the respiratory system using improvised values for resistance and elastance. This method could detect 80% of IT efforts when applied to airway signal tracings from 21 mechanically ventilated patients.

Aliasing of the airway signal with background noise may interfere with the ability of some of these methods to distinguish small deflections indicative of wasted inspiratory effort. Moreover, they may fail to identify conditions in which ventilatory support during inspiration is not sufficient to meet ventilatory requirements. Although apparently synchronous, this situation results in increased work of breathing from patient generated negative pressure efforts.

SUMMARY OF THE INVENTION

It is an object of the present invention to provide a method and system to detect respiratory asynchrony.

It is another object of the present invention to provide a non-invasive method and system to detect respiratory asynchrony.

It is a further object of the present invention to provide a method and system to detect respiratory asynchrony that does not require considerable operator experience.

It is still a further object of the present invention to provide a method and system to detect respiratory asynchrony that allows appropriate, non-asynchronous ventilatory support.

The above and other objects of embodiments of the present invention can be achieved by a method of detecting patient-ventilator asynchrony that comprises obtaining a signal representative of respiratory movement of a patient; modifying the signal in accordance with a Fourier transform to obtain a frequency spectrum of the signal; obtaining a measure of spectral organization of the obtained frequency spectrum; and providing an output signal representative of the measure.

The above and other objects of embodiments of the present invention can be achieved by a system for detecting patient-ventilator asynchrony that comprises a ventilator; a sensor operatively connected to an air output of the ventilator for providing an output representative of a characteristic of the air output; a data acquisition unit operatively connected to collect data representative of the sensor output to obtain a signal representative of respiratory movement of a patient; and a processor unit operatively connected to the data acquisition unit structured, and arranged to perform a Fourier transform of the collected data, to determine a measure of spectral organization of the transformation of the collected data, and to output a signal representative of the measure of spectral organization.

BRIEF DESCRIPTION OF THE DRAWINGS

FIGS. 4A, 4C, 4E include graphs

DESCRIPTION OF THE PREFERRED EMBODIMENTS

Figure 1:
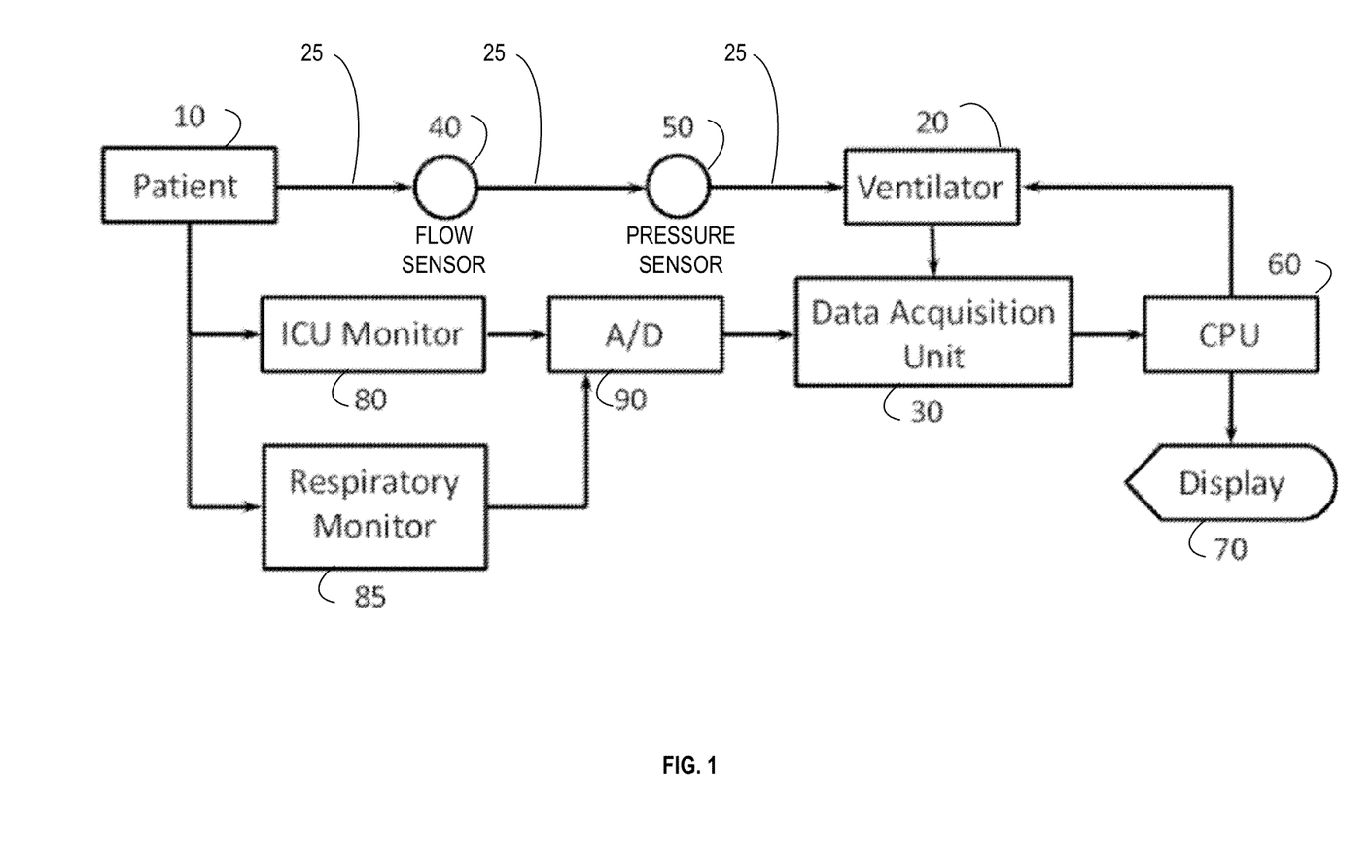
FIG. 1 is a schematic block diagram of an embodiment of a system for detecting respiratory asynchrony in accordance with the present invention.
Figure 2A:
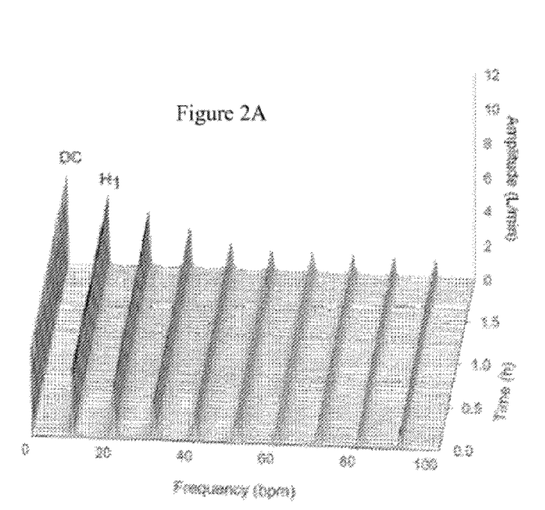
FIGS. 2A and 2B are representative graphs of frequency spectra and corresponding $H_1/DC$ values are shown in FIGS. 2C and 2D.
Figure 2B:
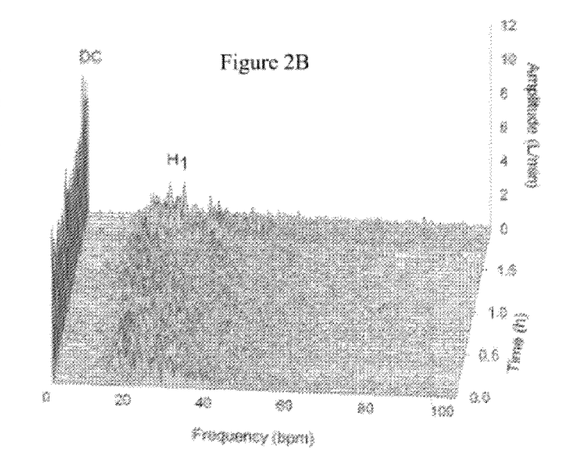
Figure 2C:
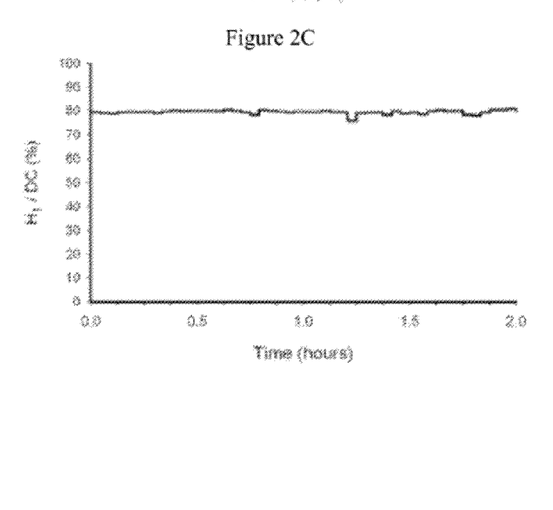
Figure 2D:
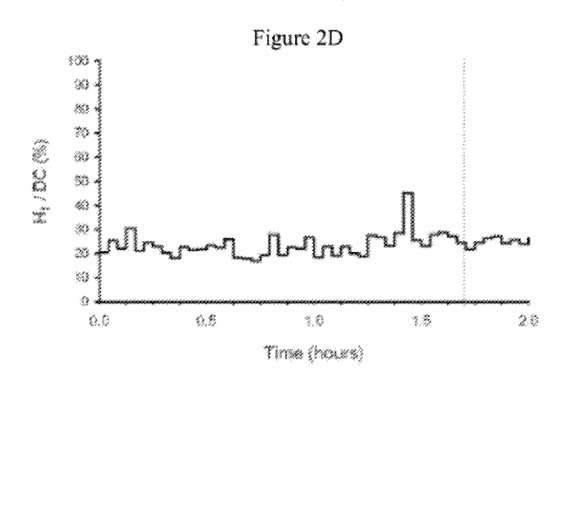
Figure 3A:
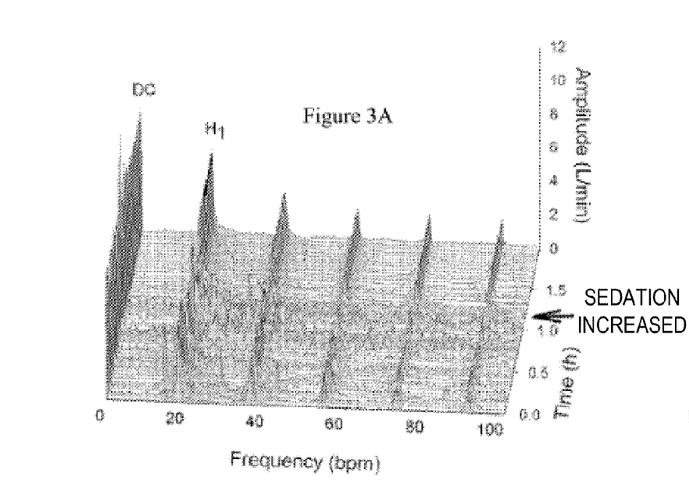
FIGS. 3A and 3B are additional representative graphs of frequency spectra and corresponding $H_1/DC$ values are shown in FIGS. 3C and 3D.
Figure 3B:
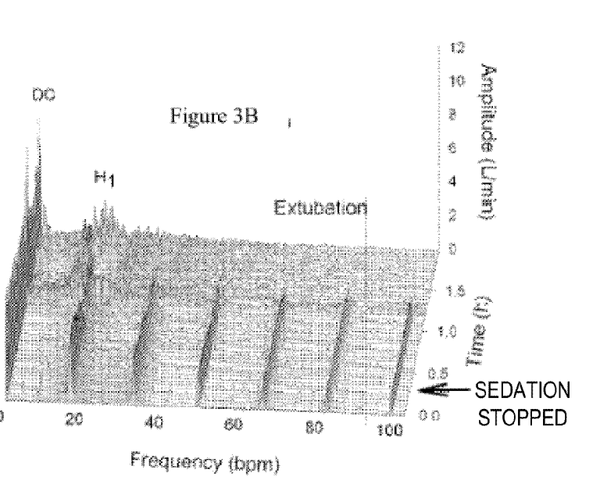
Figure 3C:
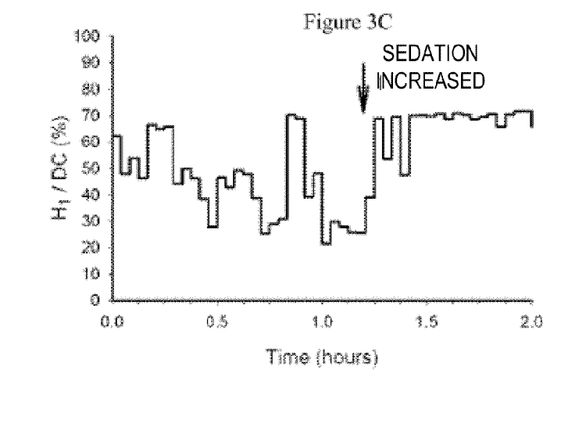
Figure 3D:
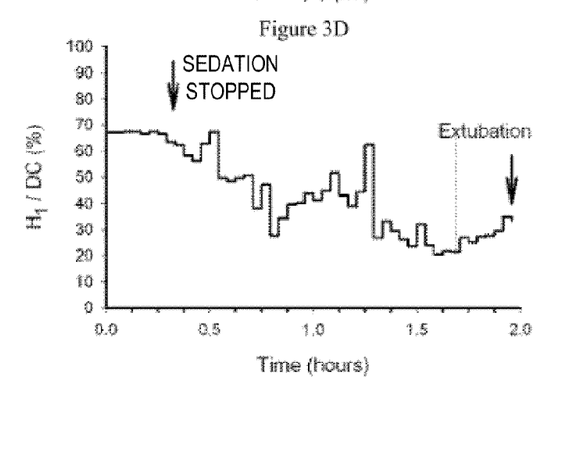
Figure 4A:
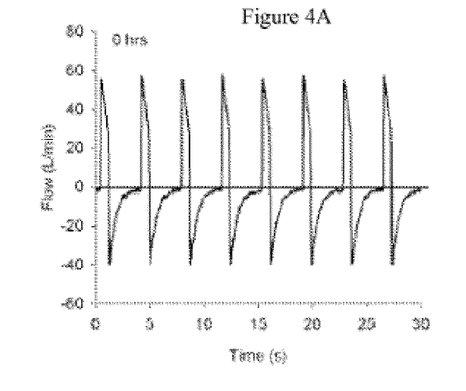
Figure 4B:
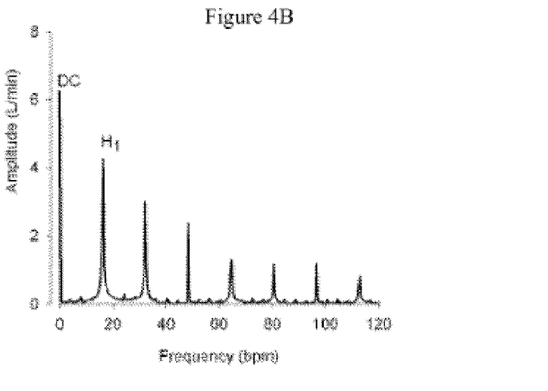
FIGS. 4B, 4D, 4F show corresponding frequency spectra for airway flow data.
Figure 4C:
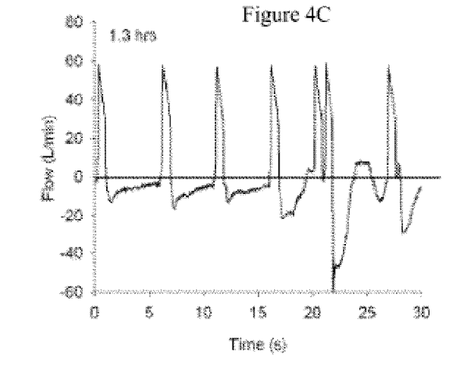
Figure 4D:
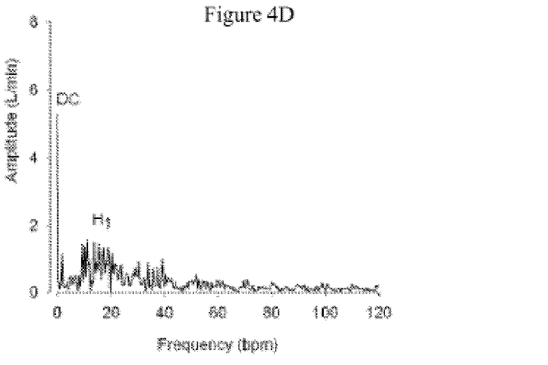
Figure 4E:
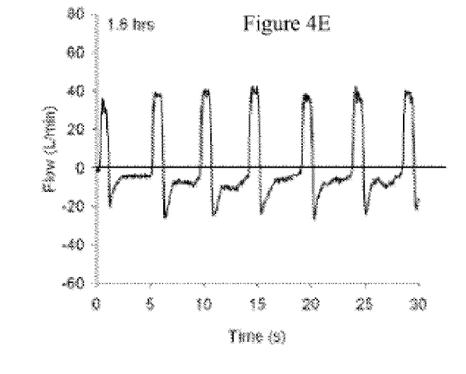
Figure 4F:
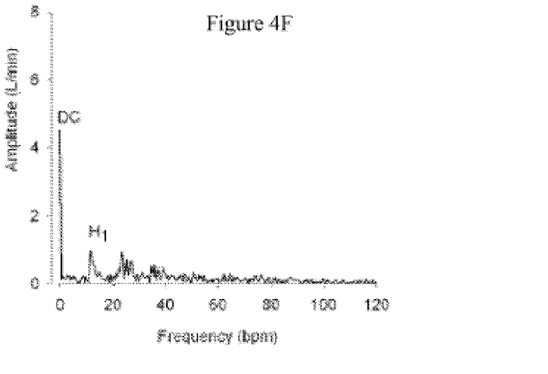

FIG. 1 is a schematic block diagram of an embodiment of a system for detecting respiratory asynchrony in accordance with the present invention. Referring to FIG. 1, in an exemplary embodiment, a patient 10 is coupled to a ventilator 20 via, for example, one or more flexible tubes or hoses 25 (not shown, but represented by the logical arrows between elements 10, 40, 50, and 20. A data acquisition system 30 acquires data such as air flow data from air flow sensor 40, air pressure d.ata from pressure sensor 50, and/or data from any other data source (e.g., sensor) such as respiratory monitor 85, or optional intensive care unit 80. Preferably such other data sources or sensors are capable of sensing any periodic signal produced by breathing, for example, motion of the chest and abdomen or air temperature changes measured with a thermistor. As shown in the illustrative embodiment of FIG. 1, the air flow sensor 40 senses the air flow provided to patient 10 via hose 25. Also as shown in FIG. 1, pressure sensor 50 senses the pressure of the air in the hose 25.

In a preferred embodiment, the ventilator can comprise a SERVO-I ventilator provided by MAQUET Critical Care A B, Solna, Sweden. This exemplary ventilator includes a built-in data acquisition system that was used as the data acquisition system 30 shown in FIG. 1. It is not necessary that a ventilator have a built-in data acquisition system. For example, a ventilator without a built-in data acquisition systems could be used together with data being monitored in analog form and digitized by a computer.

In the FIG. 1 embodiment, air flow was monitored continuously using SERVO-I ventilator built-in data acquisition system, and sampled the air flow at 30 Hz, a sampling rate exceeding the Nyquist criterion for respiratory signals. Obviously, signals can be sampled at any rate above the Nyquist rate for the signal of interest. In addition, other ventilation parameter could be collected, such as, the dynamic compliance ($C_{dyn}=V_T/$[end inspiratory pressure−PEEP]); and 3) the inspiratory resistance (Ri=[Peak pressure−plateau pressure]/ end inspiratory flow). Moreover, while the analysis in accordance with a preferred embodiment of the present invention. focuses on air flow, and pressure, any periodic physiological signals produced during human ventilation, whether or not the individual is undergoing mechanical ventilation can be used. This allows for use with invasive and non-invasive ventilation, as well as with equipment used for sleep apnea. Possible exemplary signals include airway flow, airway pressure, tidal volume, measurements of flow made with, for example, thermistors placed near the nose or mouth, measurement of rib or abdominal expansion movements made during respiration and measured by any method, including plethysmography. In other words, anything that produces a periodic signal related to respiratory movements can used to produce a spectrum for analysis in accordance with embodiments of the present invention.

Also shown in the Figure embodiment is an ICU monitor 80. An exemplary ICU monitor can be TRAM® Multi-Parameter Module, GE Healthcare Bio-Sciences Corp., Piscataway, N.J., USA. In the illustrated embodiment, the ICU monitor monitors $O_2$ saturation ($S_pO_2$), via, e.g., measured by pulse oximetry, arterial blood pressure from an arterial line; and heart rate from one electrocardiographic lead. These signals were sampled at 30 Hz rate from the analog output port of the ICU monitor (e.g., hemodynamic monitor) 80. In the illustrate embodiment being discussed here, an analog-to-digital converter 90 sampled the analog output of the ICU monitor 80 at a 30 Hz rate. One exemplary analog-to-digital converter can be, for example, a DI148U AD, provided by DATAQ Instruments, Inc. Akron, Ohio, USA. It will be recognized by those skilled in the art that while individual systems are shown in FIG. 1, they need not be individual and can be integrated. In addition, the analog-to-digital converter need not be a separate subsystem and can be integrated into a monitoring device, into a data acquisition device, or into the CPU.

Referring to the illustrative embodiment of FIG. 1, a CPU 60 receives data acquired from the ventilator 20 and the ICU monitor 80. The CPU 60 can be a laptop, a dedicated processor, a controller, or any suitable processor capable of obtaining data and performing analysis in accordance with the present invention.

In one exemplary embodiment, the CPU 80 modified the air flow data by setting all inspiratory (positive) values to zero producing a periodic signal that included only the expiratory (negative) portion of airway flow. One skilled in the art will recognize that there are other suitable approaches, such as performing a FFT on the complete signal. The CPU 80 applied the Fast Fourier Transform, which is well known those skilled in the art to the modified air flow data. P. Duhamel, Vetterli M., "Fast Fourier transforms: a tutorial review and a state of the art," *Signal Processing* 1990; 19: 259-299 provides one exemplary description of the this signal processing technique. In one embodiment the data segments include 4096 consecutive signal samples, because the method used blocks of $2^n$ samples. Each data segment comprised approximately 2.3 minutes of observation and provided sufficient information to compute a distinct frequency spectrum. The CPU 80 performed this procedure at 2.5 minute intervals, generating a total of 48 spectra during a two-hour observation period. A ratio of the first harmonic peak amplitude ($H_1$) to the amplitude of the zero frequency or DC component ($H_1$/DC ratio) was calculated for each spectrum. The AI was computed from the flow and pressure curves corresponding to the 2.3 minutes of observation to produce one spectrum.

The exemplary data shown in the accompanying figures was tested for equality of means conducted with Student's t-test with Bonferroni's correction for multiple comparisons. One-way ANOVA with post-hoc Tukey HSD test was used to compare multiple means from independent samples. The Fisher exact probability test with Pearson's correction was used to test for differences in categorical variables. The relationship between dependent variables was determined with linear regression analysis. The figures are shown as mean±SD. A $p<0.05$ was considered significant.

Figure 8:
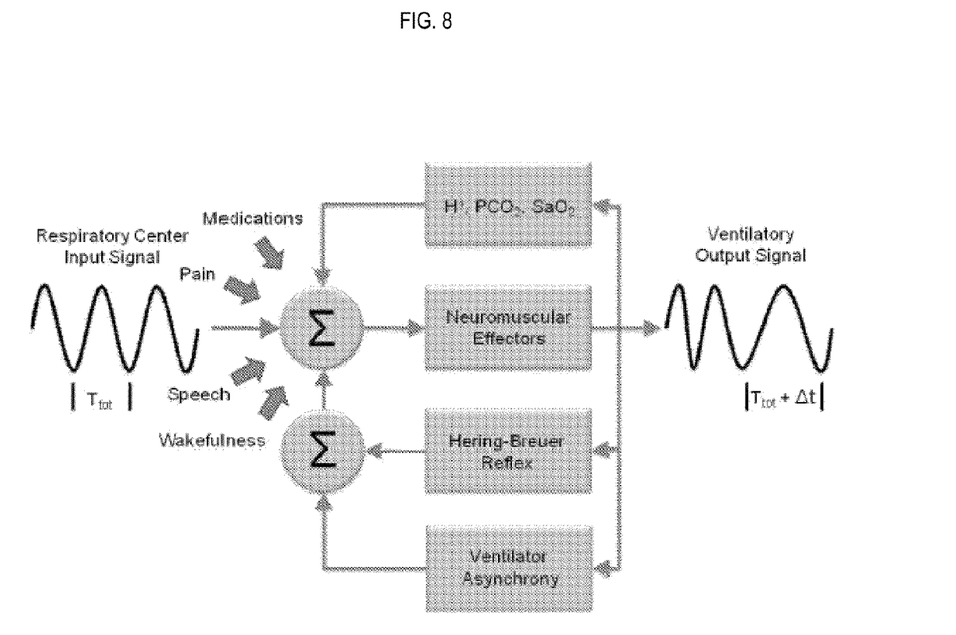
FIG. 8 is a generalized schematic diagram of parameters influencing the frequency of respiration.

FIG. 8 is a schematic diagram illustrating some exemplary frequency components of a ventilator signal, such as the signal processed in accordance with embodiments of the present invention. The precise cellular and molecular mechanisms that generate and modulate respiratory rhythm remain unknown, it is useful to think of an idealized respiratory center input signal as having a nearly constant periodicity shown here as the time taken to complete one full breath cycle, $T_{Tot}$. Cortical inputs, among them the degree of alertness, speech, pain, etc, modify the respiratory center input signal as it activates the neuromuscular effectors to produce a ventilatory output signal. The periodicity of this output signal is no longer constant, as $T_{Tot}$ is now altered by variations in time ($\Delta t$) that may have either positive or negative values from breath to breath. Feedback loops, among them mechanical output of respiratory muscles, peripheral chemoreceptors, and the Hering-Breuer mechanoreceptor reflex modulate the respiratory control of breathing. Under normal conditions $\Delta t$ is small, imparting the respiratory cycle its inherent timing variability. Mechanical ventilation adds an additional feedback control that modulates breathing pattern. It is our hypothesis that asynchronous events during mechanical ventilation modify the Hering-Breuer reflex, increasing $\Delta t$ on a breath-by-breath basis and greatly augmenting $T_{Tot}$ variability. These changes in $T_{Tot}$ are difficult to detect from direct examination of airway signal tracings.

Embodiments of the present invention use a parameter, $H_1$/DC, to characterize the frequency spectral pattern. Such a parameter represents a measure of spectral organization. Other parameters reflective of spectral organization can be used, such as, for example, H2/DC, H3/DC, H2/H1, coherence function etc. In other words, any pattern recognition scheme to determine the degree of peak sharpness can be used as an indication of spectral organization; and thus to indicate the presence of asynchrony. While the following discussion of one exemplary embodiment focuses on $H_1$/DC, it is not intended to limit the invention to a specific measure of spectral organization, or disorganization.

Figure 5:
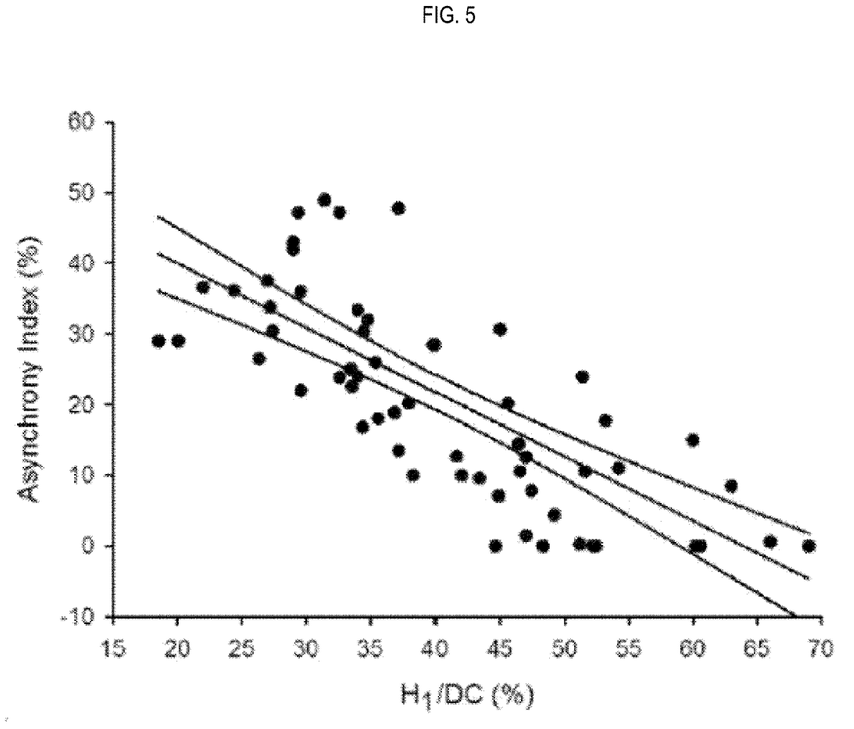
FIG. 5 is a graph illustrating representative data correlating $H_1/DC$ values with patient-ventilator asynchrony.
Figure 6A:
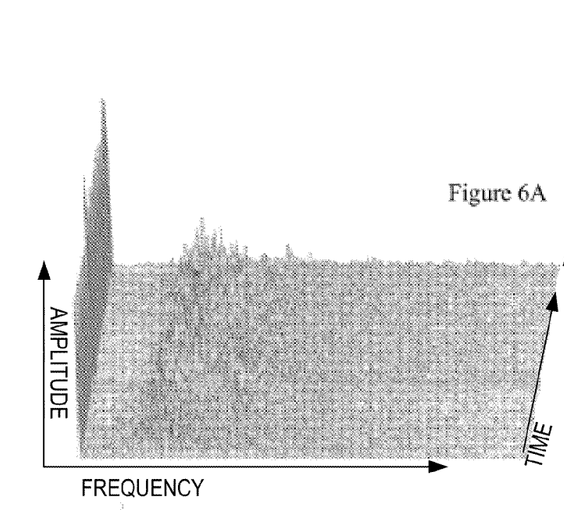
FIGS. 6A-6D are representative graphs of frequency spectra for various identified types of frequency spectra.
Figure 6B:
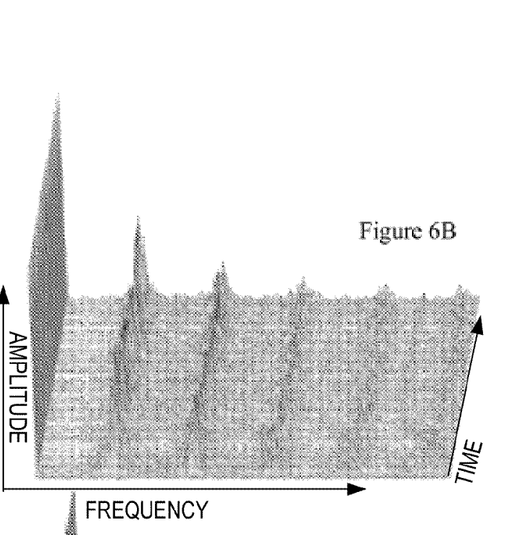
Figure 6C:
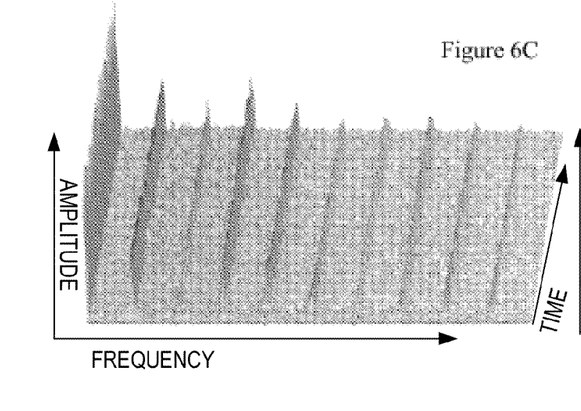
Figure 6D:
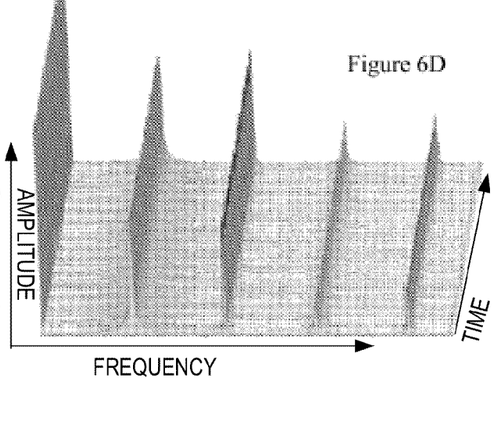

In embodiments using $H_1$/DC, greater $H_1$/DC values corresponded to more organized spectral patterns and were usually seen in what appeared to be better synchronized patients. These observations were confirmed by assessing patient-ventilator asynchrony using the AI method in which an inverse correlation was found between AI and $H_1$/DC. The AI method lacks sensitivity and is prone to observer associated errors, which may explain the dispersion noted when correlating AI to $H_1$/DC, such as shown in FIG. 5. In addition, the strength of the correlation (r=0.74) supports the association of decreases in $H_1$/DC with greater patient-ventilator asynchrony.

The use of the parameter $H_1$/DC to characterize the frequency spectral pattern has a solid physiological foundation. For example, the DC amplitude corresponds to mean expiratory flow and the $H_1$ peak is located at the frequency corresponding to the average respiratory rate for the period of observation. In embodiments of the present invention, a $H_1$/DC of approximately 45%, and in particular 43%, is used to differentiate organized from disorganized spectral patterns with a high degree of sensitivity and specificity.

In view of the above, embodiments of the present invention utilize $H_1$/DC as a non-invasive parameter of asynchrony, with $H_1$/DC of approximately less than 45% (e.g., 43%) serving as cutoff for patients having difficulties entraining to the ventilator. While it is possible that different ventilatory modes could alter the frequency spectra of airway signals; an embodiment discussed herein substantially eliminates that possibility by using only the expiratory portion of the flow signal. As modified, this flow signal reflects only patient related physiology, be it passive expiration or forced expiratory efforts, and is independent of the method employed to insufflate the lungs. This modification is, however, not essential to the present invention and other embodiments without this modification can be used.

In accordance with embodiments of the present invention, spectral patterns are determined and can be displayed on a display 70 for modification of ventilation. Obviously, a totally disorganized pattern (Type 1) indicates severe asynchrony, a condition known to be detrimental to patients, and indicates that ventilation adjustment is needed. On the other hand, normal physiological systems carry some degree of noise[32] and a highly organized spectral pattern (Type 4) also may not be desirable, as it could indicate other conditions that adversely affect outcome[33] such as the excessive use of sedatives and neuromuscular blockade.

The Fourier frequency analysis utilized in embodiments of the present invention provides an indication of breath-by-breath alterations in $T_{Tot}$. The exemplary embodiments herein use $T_{Tot}$ as the main determinant of spectral pattern. In other words, as breath-by-breath variation in $T_{Tot}$ increases, airflow frequency spectra shift from a highly organized to a disorganized pattern. Applying a Fourier frequency analysis to the data provides a correlation between such changes and patient-ventilator asynchrony and allows detection of patient-ventilator asynchrony. Changes in $T_{Tot}$ are difficult to detect when examining the time dependent airflow signal but are apparent when presented as a frequency spectrum. As discussed below, different spectral patterns correlated with the degree of sedation and patient-ventilator asynchrony. Patients who were well synchronized with the ventilator displayed a spectral pattern composed of sharp Gaussian-shaped peaks, monotonically spaced at frequency multiples of the respiratory rate. This spectral pattern indicates a nearly perfect patient-ventilator coupling. As patient-ventilator asynchrony increases, the frequency spectra evolves into a more chaotic pattern, one in which the bandwidth of the Gaussian-shaped peaks widens, their amplitudes decrease, and higher frequency harmonics disappear.

FIG. 2 shows a frequency spectra corresponding to two patients who, as judged by the AI, had very different levels of asynchrony. The 48 spectra obtained during the two-hour observation period are arranged in the form of a staggered ensemble beginning with the first spectrum. Patient A was a 63 y/o woman being ventilated through an endotracheal tube with clinical and radiological signs of brain death. The patient was perfectly coupled to the ventilator with an AI of zero. The spectra are characterized by sharp Gaussian-like peaks located at multiples of the fundamental frequency, or mean respiratory rate of 10.0±0.0 breaths per minute (bpm). Each spectrum repeats almost exactly every 2.5 minutes. Patient B was a 68 y/o woman ventilated through a tracheostomy with several failed attempts at weaning She was fully awake during the period of observation and appeared to be poorly synchronized with the ventilator, as evidenced both by direct observation and an AI of 46%. The spectra are highly disorganized with broadly based and poorly defined $H_1$ peaks centered at the respiratory rate of 20.2±4.6 bpm. The spectra also lack subsequent harmonic peaks. Both spectral ensembles had measureable DC components corresponding to the mean of the expiratory flow signal (5.2±0.1 L/min for patient A; 7.3±0.8 L/min for patient B, respectively; p<0.01). FIG. 2 also shows changes in the $H_1/DC$ ratio corresponding to the spectral ensembles. During the two-hour observation period this ratio was approximately constant at 79.5±0.8% for patient A, but was lower and had greater variability for patient B at 23.8±4.5% (p<0.001).

The frequency ensembles from most of the observed patients showed spectral patterns falling somewhere between those of FIG. 2, at times even displayed characteristics of both patterns during the two hour observation period. This is illustrated in FIG. 3 where an 88 y/o woman with congestive heart failure (Patient C) became increasingly uncomfortable on the ventilator during the period of observation. This was associated with decreasing spectral organization and a decline in the $H_1/DC$ ratio from an initial value of 62% to a nadir of 22% after one hour of observation. As the i.v. dose of the sedative fentanyl was doubled, the frequency spectra reverted to the Gaussian-peak pattern with a rise in $H_1/DC$ to 70%. A different spectral progression was seen when monitoring Patient D, a 52 y/o man admitted to the ICU following coronary artery bypass surgery. The patient's i.v. sedation was discontinued shortly after beginning data recording and he was extubated two hours later. Expiratory flow spectra initially showed a distinct Gaussian-peak pattern, with $H_1$ located at respiratory rate of 16 bpm and $H_1/DC$ ratio of 67%. The patient's spectra became progressively disorganized as sedation wore off, with decreases in $H_1/DC$ ratio to 20%-30% just prior to extubation.

FIG. 4 shows the complete flow signals for patient D of FIG. 3 measured at times zero, 1.3 hours and 1.6 hours, along with the frequency spectra of the expiratory flow. Airway flow at time zero shows near perfect patient-ventilator synchronization corresponding to a highly organized spectrum having sharp Gaussian peaks at frequencies multiple of the respiratory rate (16.3 bpm; $H_1/DC=67\%$). At 1.3 hours the flow signal shows signs of asynchrony, characterized by double triggering. This was associated with an extremely disorganized frequency spectrum with a broadly based $H_1$ centered at 14.5 bpm, loss of subsequent harmonic peaks and $H_1/DC$ of 29%. The expiratory flow signal at 1.6 hours shows more subtle signs of asynchrony, such as increases in end-inspiratory flow and the initiation of ventilator-driven inspiratory effort prior to end-expiration, with the possible development of dynamic hyperinflation. Although at first glance this flow signal appears to be more regular than the previous one, subtle breath-by-breath alterations in $T_{Tot}$ resulted also in a disorganized spectral pattern with $H_1/DC$ of only 21%.

In addition to the above, the AI from the airway signals and $H_1/DC$ from the expiratory flow frequency spectrum at observation times 0, 30, 60, 90 and 120 minutes were obtained, and their average values calculated. FIG. 5 shows individual mean AI plotted as a function of the corresponding mean $H_1/DC$ for all patients in the study (n=66). There was a strong inverse relationship between AI and $H_1/DC$ (AI=58.2−0.9 $H_1/DC$; $r^{2=0.54}$, p<0.001) supporting the notion that decreases in $H_1/DC$ are associated with increases in patient-ventilator asynchrony.

Figure 7:
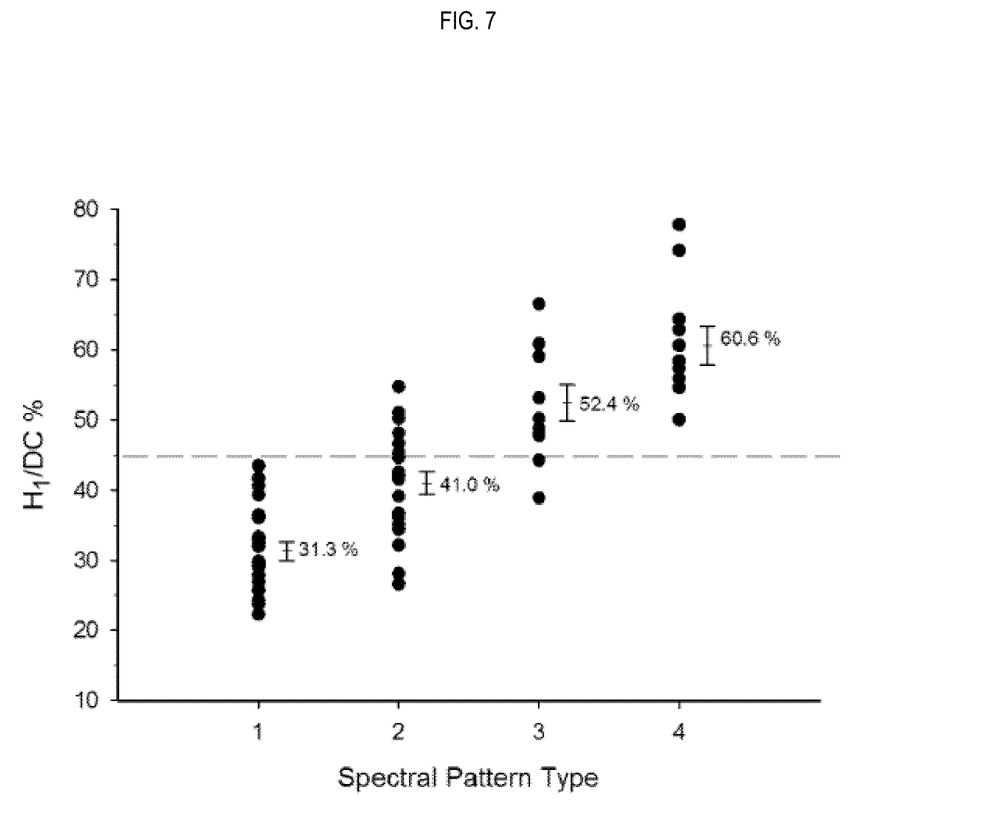
FIG. 7 is a representative graph correlating frequency spectra types and $H_1/DC$.

With the aim of developing an objective method to classify spectral patterns according to their degree of organization, numerical values from 1 to 4 are assigned to the spectral ensembles shown in FIG. 6. These values range from poorly organized (Pattern 1) to highly organized (Pattern 4). Eighteen independent observers were instructed to classify each two-hour spectral ensemble from the present study (n=66) according to the patterns shown in FIG. 6. The mode of the 18 values assigned to each ensemble by the independent observers were calculated. The average $H_1/DC$ from the 48 spectra for each two-hour ensemble was also calculated. FIG. 7 shows the mode of the observers' classification plotted as a function of the average $H_1/DC$ ratio.

All spectral ensembles classified as pattern 1 had $H_1/DC<45\%$, whereas all those classified as pattern 4 had $H_1/DC\geq45\%$. Also shown in FIG. 7 are the mean±95% confidence limits for $H_1/DC$ corresponding to each spectral pattern type. There is clear relationship between spectral pattern type and $H_1/DC$, with each type pattern separated by an increment in $H_1/DC$ of approximately 10%. When combining patterns 1 and 2 into a "disorganized" group and patterns 3 and 4 into an "organized" group, a $H_1/DC$ of approximately 45% or greater differentiated them with a sensitivity of 84.1% and a specificity of 91.3%. The close relationship between the spectral pattern and H1/DC allows for display of H1/DC as a measure of asynchrony at 2.5 minute intervals.

The above shows that obtaining the frequency spectra provides a useful indication of patient-ventilator asynchrony. Display of H1/DC allows for careful adjustment of a ventilator to correct and eliminate or reduce patient-ventilator asynchrony. Obtaining $H_1/DC$ provides a useful indicator of detecting patient-ventilator asynchrony. Display of the $H_1/DC$ also allows careful adjustment of a ventilator to correct and eliminate or reduce patient-ventilator asynchrony. Moreover, outputting a signal corresponding to $H_1/DC$ by the CPU 60 to the ventilator 20 allows automatic adjustment of the ventilator to correct for patient-ventilator asynchrony based on the calculated $H_1/DC$ in accordance with the present invention.

The measure of spectral organization, such H1/DC or the others mentioned above, or information derived therefrom, can alert for the presence of asynchrony to physicians and nurses caring for the patient so that therapeutic measures may be taken. Measures can include, for example, manual changes in ventilator settings, such as the respiratory rate and ventilation. volumes. Other therapy could be greater sedation or the use of paralytic agents. It also possible to utilize the information provided by H1/DC to make ventilator changes automatically, through the use of a feedback system aimed at maintaining the level of patient-ventilator asynchrony within a desired range. As will be recognized to those skilled in basic feedback control, the CPU 60 could be programmed to compute the difference ($\Delta$H1/DC) between the measured H1/DC and a previously set point (desired) for H1/DC and use difference ($\Delta$H1/DC) as a feedback signal to make changes on the mechanical ventilator 20 such as schematically illustrated in the exemplary feedback system shown in FIG. 9.

Figure 9:
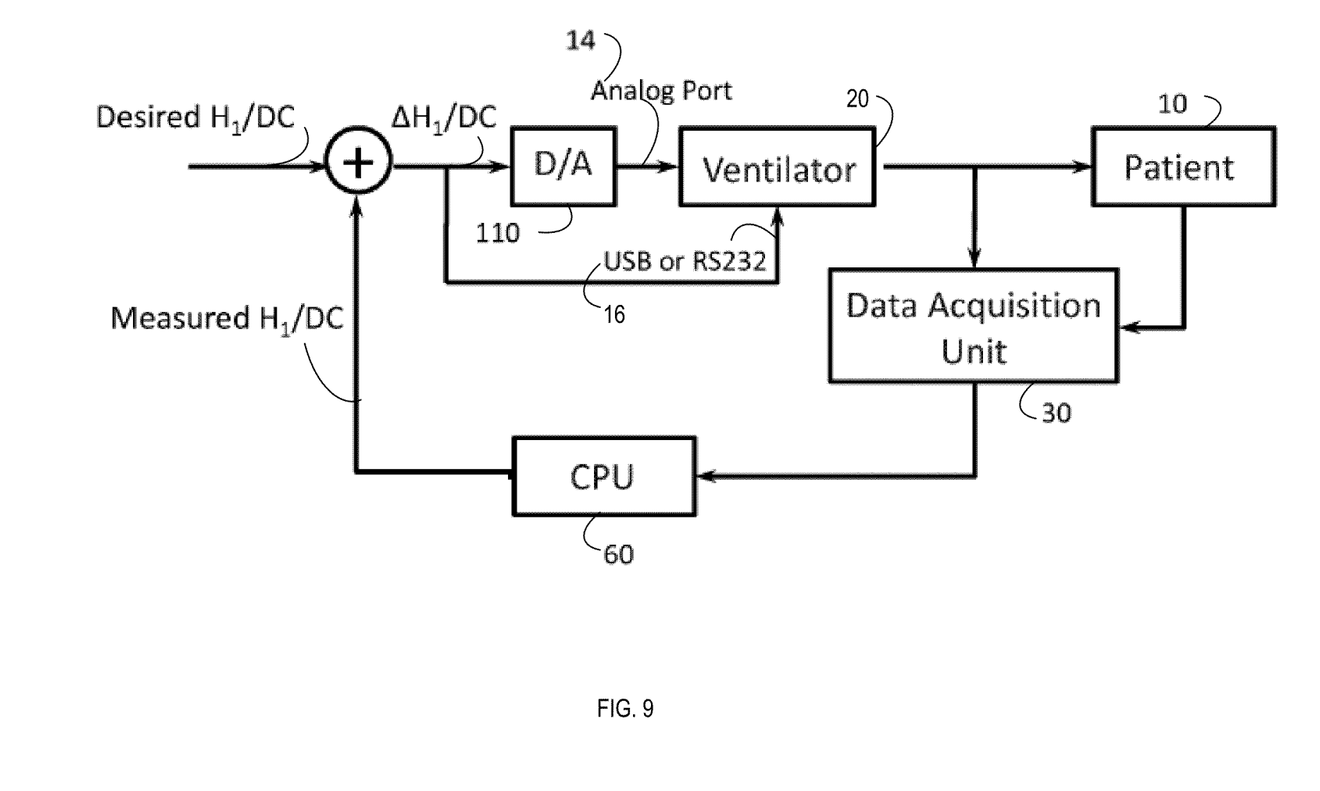
FIG. 9 schematically illustrates an exemplary ventilator feedback system.

In an exemplary feedback system such as shown in FIG. 9, the feedback signal (e.g., $\Delta$H1/DC) is applied to the ventilator 20. As shown, the feedback signal can be applied either as an analog voltage to an analog port 14 using a digital-to-analog converter 110 or as a digital signal delivered to an input port 16 such as a USB port or a RS232 port of the ventilator 20. For example, if decreases in H1/DC below a set value, for example 40% are determined by the CPU 60, the CPU 60 can send a signal to the ventilator 20 to change inspiratory volume delivered or in the number of breaths. The ventilator 20 also could be programmed to switch from one mode of ventilation, for example, pressure controlled mode to another, such as volume controlled mode.

The invention claimed is:

1. A method of detecting patient-ventilator asynchrony comprising:
    obtaining, by at least one processor, a flow or pressure signal representative of respiratory movement of a patient on ventilatory support of a mechanical ventilator, captured by at least one respiratory sensor;
    modifying, by the at least one processor, the flow or pressure signal comprising:
        taking at least a portion of the flow or pressure signal; and
        transforming said at least said portion of the flow or pressure signal in accordance with a Fourier transform to obtain a frequency spectrum of said at least said portion of the flow or pressure signal;
    obtaining, by the at least one processor, a measure of spectral organization wherein said spectral organization comprises a spectral pattern of recurrent peaks of the obtained frequency spectrum;
        wherein said obtaining the measure of spectral organization comprises:
            obtaining, by the at least one processor, a ratio of a harmonic peak amplitude to an amplitude of a direct current (DC) component of said at least said portion of the flow or pressure signal,
            said obtaining said ratio comprising:
                dividing, by the at least one processor, the harmonic peak amplitude, by the amplitude of the DC component of said at least said portion of the flow or pressure signal; and
    providing, by the at least one processor, at least one of an output, or an output signal representative of the measure.

2. The method of detecting patient-ventilator asynchrony according to claim 1,
    wherein the obtaining a measure of spectral organization comprises obtaining a coherence function of the obtained frequency spectrum.

3. The method of detecting patient-ventilator asynchrony according to claim 1, wherein said providing said at least one of said output or said output signal comprises at least one of:
    displaying or providing, by the at least one processor, a value corresponding to the measure;
    displaying or providing, by the at least one processor, an indication associated with a value of the measure; or
    displaying or providing, by the at least one processor, at least one alert associated with a value of the measure.

4. The method of detecting patient-ventilator asynchrony according to claim 1, wherein said providing said at least one of said output or said output signal comprises at least one of:
    displaying, or providing, by the at least one processor, the frequency spectrum of the signal;
    displaying or providing, by the at least one processor, an indication associated with the frequency spectrum of the signal; or
    displaying or providing, by the at least one processor, at least one alert associated with the frequency spectrum of the signal.

5. The method of detecting patient-ventilator asynchrony according to claim 1, wherein said providing said at least one of said output or said output signal comprises at least one of:
    providing an indication to adjust, by the at least one processor, the mechanical ventilator to adjust patient-ventilator asynchrony in response to at least one of the output signal, or the measure of spectral organization;
    providing an indication to adjust, by the at least one processor, the mechanical ventilator to increase patient-ventilator asynchrony in response to at least one of the output signal, or the measure of spectral organization; or
    providing an indication to adjust, by the at least one processor, the mechanical ventilator to decrease patient-ventilator asynchrony in response to at least one of the output signal, or the measure of spectral organization.

6. The method of detecting patient-ventilator asynchrony according to claim 1,
    wherein the flow or pressure signal represents at least one of:
        airway flow,
        airway pressure,
        tidal volume,
        measurements of flow made with at least one thermistor placed near at least one of a nose, or a mouth of the patient, or
        measurement of at least one of rib or abdominal expansion movement of the patient made during respiration by the patient on the ventilator.

7. The method according to claim 1, wherein the harmonic peak amplitude comprises at least one of:
    an amplitude height of a first harmonic peak of the frequency spectrum of the flow or pressure signal; or
    an area under a first harmonic peak of the frequency spectrum of the flow or pressure signal.

8. The method according to claim 1, wherein said at least said portion comprises at least one of:
    an inspiratory portion of the flow signal;
    an expiratory portion;
    or at least a portion of said pressure signal.

9. The method according to claim 1, wherein said at least said portion comprises at least one of:
    an expiratory portion, representing patient effort; or
    at least a portion of the amplitude of the at least a portion of flow signal or pressure signal.

10. The method according to claim 1, further comprising at least one of:
    providing at least one of an alert or an indication to adjust sedation;
    providing at least one of an alert or an indication to adjust use of at least one paralytic agent; or
    providing at least one of an alert or an indication to adjust ventilatory support.

11. A system for detecting patient-ventilator asynchrony comprising:

at least one sensor operatively coupled to an air output of a mechanical ventilator for providing a sensor output representative of a characteristic of the output flow or pressure;

at least one data acquisition unit operatively coupled to said at least one sensor to collect time dependent data representative of the sensor output flow or pressure to obtain a time dependent signal representative of respiratory movement of a patient;

at least one processor operatively coupled to said at least one data acquisition unit,
wherein said at least one processor is adapted to:
take at least a portion of the flow or pressure,
transform said at least said portion of the flow or pressure comprising wherein said at least one processor is adapted to:
perform a Fourier transform of the collected time dependent data to determine a measure of spectral organization of the transformation of the collected time dependent data,
wherein to determine the measure of spectral organization of the transformation comprises wherein said at least one processor is adapted to:
determine a ratio of a harmonic peak amplitude to an amplitude of a direct current (DC) component of said at least said portion of the flow or pressure of the measure of spectral organization of the transformation of the collected time dependent data, and
wherein said at least one processor is adapted to:
provide, or output data indicative of a signal representative of the measure of spectral organization.

12. The system for detecting patient-ventilator asynchrony according to claim 11,
wherein the measure of spectral organization comprises:
wherein said at least one processor is adapted to determine a coherence function of the transformation of the collected data.

13. The system for detecting patient-ventilator asynchrony according to claim 11,
wherein the at least one sensor comprises at least one:
a flow sensor;
a respiratory sensor;
a pressure sensor;
a mechanical ventilator; or
a ventilator.

14. The system for detecting patient-ventilator asynchrony according to claim 11, further comprising at least one of:
a heart monitor operatively coupled to provide heart rate data to the data acquisition unit; or
a patient monitor operatively coupled to a patient to provide patient data to the data acquisition unit.

15. The monitoring system according to claim 11, further comprising at least one of:
a mechanical ventilator;
a respiratory monitor;
a positive pressure mechanical ventilator;
an intensive care unit (ICU) monitor; or
a hemodynamic monitor.

16. A method of detecting patient-ventilator asynchrony comprising:
obtaining, by at least one processor, a flow or pressure signal representative of respiratory movement of a patient on ventilatory support of a mechanical ventilator, captured by at least one respiratory sensor;
modifying, by the at least one processor, the flow or pressure signal comprising:
taking at least a portion of the flow or pressure signal; and
transforming said at least said portion of the flow or pressure signal in accordance with a Fourier transform to obtain a frequency spectrum of said at least said portion of the flow or pressure signal;
obtaining, by the at least one processor, a measure of spectral organization wherein said spectral organization comprises a spectral pattern of recurrent peaks of the obtained frequency spectrum;
wherein said obtaining the measure of spectral organization comprises:
obtaining, by the at least one processor, a ratio of a harmonic peak amplitude to an amplitude of a direct current (DC) component of said at least said portion of the flow or pressure signal,
wherein said obtaining said ratio comprises:
dividing, by the at least one processor, the harmonic peak amplitude, by the amplitude of the DC component of said at least said portion of the flow or pressure signal;
providing, by the at least one processor, at least one of an output, or an output signal representative of the measure,
wherein said providing further comprises at least one of:
providing at least one of an alert or an indication to adjust sedation;
providing at least one of an alert or an indication to adjust use of at least one paralytic agent;
providing at least one of an alert or an indication to adjust ventilatory support;
providing at least one of an alert or indication to adjust a dose of sedative;
providing at least one of an alert or indication to discontinue sedation;
providing at least one of an alert or indication to increase sedation;
providing at least one of an alert or indication to decrease sedation;
providing at least one of an alert or indication to adjust a neuromuscular blocking therapeutic measure;
providing at least one of an alert or indication to adjust a paralytic agent; or
providing at least one of an alert or indication to adjust the mechanical ventilator.

* * * * *